US008352021B2

(12) United States Patent
Scheib (10) Patent No.: US 8,352,021 B2
(45) Date of Patent: Jan. 8, 2013

(54) METHOD AND SYSTEM FOR JOINTLY MONITORING PHYSIOLOGICAL CONDITIONS

(76) Inventor: Christopher Scheib, Nicholasville, KY (US)

( * ) Notice: Subject to any disclaimer, the term of this patent is extended or adjusted under 35 U.S.C. 154(b) by 754 days.

(21) Appl. No.: 12/589,047

(22) Filed: Oct. 16, 2009

(65) Prior Publication Data

US 2010/0113960 A1 May 6, 2010

Related U.S. Application Data

(63) Continuation-in-part of application No. 12/082,842, filed on Apr. 15, 2008, now Pat. No. 7,720,531.

(60) Provisional application No. 61/196,247, filed on Oct. 16, 2008.

(51) Int. Cl.
*A61B 5/04* (2006.01)

(52) U.S. Cl. ........................................ 600/544; 600/545

(58) Field of Classification Search .................. 600/300, 600/544, 545, 26; 340/575–576
See application file for complete search history.

(56) References Cited

U.S. PATENT DOCUMENTS 5,813,993 A * 9/1998 Kaplan et al. ................. 600/544

* cited by examiner

*Primary Examiner* — Michael Kahelin
*Assistant Examiner* — Michael D'Angelo
(74) *Attorney, Agent, or Firm* — Stockwell & Smedley, PSC (57) ABSTRACT

A method for providing an indication of a state of awareness for a patient, includes the steps of arranging data of an EEG and EMG power spectrogram to provide power versus frequency in a log-log arrangement; calculating a first best-fit line for a lower frequency region of the EEG power spectrogram; calculating a second best-fit line for a higher frequency region of the EEG power spectrogram; calculating a third best-fit line for the EMG power spectrogram; and displaying an indication of the state of awareness based on the first, second and third best-fit lines.

25 Claims, 8 Drawing Sheets

METHOD AND SYSTEM FOR JOINTLY MONITORING PHYSIOLOGICAL CONDITIONS

RELATED APPLICATIONS

The present invention is a continuation-in-part of the previously filed U.S. patent application Ser. No. 12/082,842 filed Apr. 15, 2008, the disclosure of which is incorporated herein in its entirety. Priority is claimed, as well, to the provisional patent application Ser. No. 61/196,247 filed Oct. 16, 2008, the disclosure of which is incorporated by reference in its entirety.

BACKGROUND

Field

The present invention relates generally to monitoring brain function during different states of consciousness such as general anesthesia, coma or natural sleep and, more particularly, to using electroencephalogram (EEG) data and other physiological data to evaluate brain function.

The central nervous system (CNS) in the anesthetic state commonly responds to surgical manipulations at the spinal cord and brainstem levels without the patient regaining consciousness. This can result in stress responses and possibly increased pain after the surgery. These CNS responses also interfere with interpreting the EEG as a measure of the anesthetic state. Thus, there remains a need for a method of interpreting the anesthetic state of a patient which accounts for the effects that may be caused by patient responses other than those measured with an EEG.

SUMMARY

The present invention relates to a method for providing an indication of a state of awareness for a patient, that includes the steps of arranging data of an EEG and EMG power spectrogram to provide power versus frequency in a log-log arrangement; calculating a first best-fit line for a lower frequency region of the EEG power spectrogram; calculating a second best-fit line for a higher frequency region of the EEG power spectrogram; calculating a third best-fit line for the EMG power spectrogram; and displaying an indication of the state of awareness based on the first, second and third best-fit lines.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Various aspects of a system and method for anesthesia monitoring are illustrated by way of example, and not by way of limitation, in the accompanying drawings, wherein.

DETAILED DESCRIPTION OF THE PREFERRED EMBODIMENTS

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1:
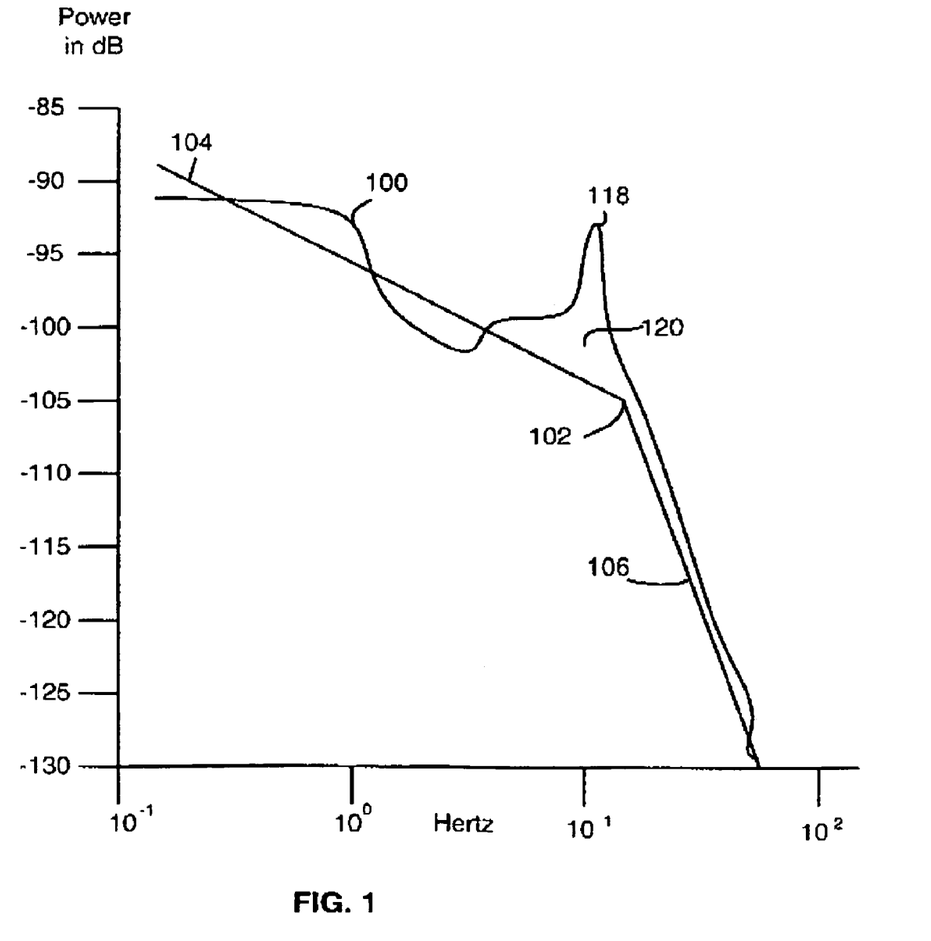
FIG. 1 shows an exemplary log-log EEG power spectrogram in accordance with the principles of the present invention.

In the above-incorporated patent applications the frequency range of contemplated signals extended to about 40 Hz. FIG. 1 shows an exemplary log-log EEG power spectrogram in accordance with the principles of the referenced, incorporated patent application. The spectrogram 100 is that of a patient that is deeply under anesthesia. In other words, the patient has crossed the transition point into a lack of awareness and is relatively far from returning to that transition point. As shown, the power of frequencies above about 12 or 15 Hz significantly drops while the power at the lower frequencies is much higher. In accordance with providing the information in a log-log format, the spectrogram 100 can be transformed into the best-fit lines 104, 106. Regardless of the point of reference from which you measure, the respective slopes of the low frequency line 104 and the high frequency line 106 are vastly different. The intersection point 102 is at about 15 Hz. As noted, this display allows for simple analysis of the anesthetic state, or more generally, the brain function, of a patient.

Additional useful data can be extracted from the graph depicted in FIG. 1. In this graph, an alpha peak 118 is present that would typically be considered an outlier when calculating the best fit line 104. Other peaks may occur in the EEG signal 400 and may be useful as well. One beneficial analysis of such peaks is to use the best fit line 104 as a baseline and subtract it from the signal 100. For the alpha peak 118, for example, the area 120 above the baseline represents information about the alpha peak. For example, its amplitude, its spread, and the center frequency can all be determined by analyzing the area 120. Regression analysis of these parameters revealed that there is a correlation between the alpha peak frequency and concentration of the anesthetic agent. Thus, because the alpha peak generally shifts with concentration of anesthesia (decreasing frequency as concentration increases), the changes in the alpha peak can be used as additional information or confirmation when making a determination about the state of awareness of the patient. In some tests, surgical stimulation (e.g., retracting an inflamed nerve root) also resulted in changes of the alpha peak size and location such as reducing the amplitude of the alpha peak and/or shifting it to a higher or lower frequency. These additional factors may be useful when determining the state of awareness of the patient.

However, additional investigation has established that extending the frequency range to about 130 Hz provides beneficial data and analysis as well. Going from 40 Hz to 130 Hz goes beyond what is traditionally thought of as EEG into the EMG range. Similarly, as before, the EEG (and now EMG) data is plotted in a log-log representation. This representation and extended frequency range allows more than two best-fit lines to be calculated. For example, the raw data can be modeled by 3, 4 or even more best-fit lines. Once these lines are calculated, analysis of the lines can occur. Within this patent application, the terms EEG and EMG are used for convenience to refer to sensing and collecting physiological responses in the frequency ranges from about 0 Hz to about 130 Hz. Use of these terms is not intended to limit the scope of the present invention to only EEG or EMG machines or techniques but, instead, is intended to encompass sensing of the electrical physiological responses produced by a person within the specified frequency range.

The differences in the heights and slopes of each line, the frequency and amplitude of the intersection points, and the angles formed at the intersections all provide useful data in evaluating brain function.

In addition, the presence and location of various peaks in the log-log data are useful as well. The frequency at which the alpha peak and the delta peak occur, for example, provide useful information for evaluating brain function. When used in conjunction with the best-fit line data, the peak locations provide further certainty that the analysis of brain function is accurate. The area under the peak and a corresponding best-fit line is useful as well. The more the peak spreads or the higher the peak is, generally the more area that will be under the peak which is useful information for evaluating brain function.

In one particular example, there is a correlation between the alpha peak frequency and concentration of the anesthetic agent. Thus, data about the alpha peak (e.g., frequency, height, area, etc.) are indicators of brain function in the presence of an anesthetic agent.

It is also known that surgical stimulation may routinely cause changes of the alpha peak size and location such as increasing or decreasing the amplitude of the alpha peak and/or shifting it to a higher or lower frequency. These additional factors may be useful when determining the state of awareness of the patient. As such, there is a pattern to the peaks that changes as anesthetic agent concentration changes and there is a pattern to the peak width that changes as anesthetic agent concentration changes, as well.

The combined EEG-EMG spectrogram is produced by several neurophysiologic processes. The combination of baseline analysis (with the log-log relationship) and the detection of oscillation processes (with peaks and areas above the baseline) are able to measure the contributions of each of the several neurophysiologic processes. This combined method is required to assess the multiple central nervous system (CNS) responses to surgery when in the anesthetic state.

The CNS in the anesthetic state commonly responds to surgical manipulations at the spinal cord and brainstem levels without the patient regaining consciousness. This can result in stress responses and possibly increased pain after the surgery. These CNS responses also interfere with interpreting the EEG as a measure of the anesthetic state. The combined EEG-EMG approach described herein can help the anesthesia clinician make adjustments in the amount of the different agents used.

Figure 2:
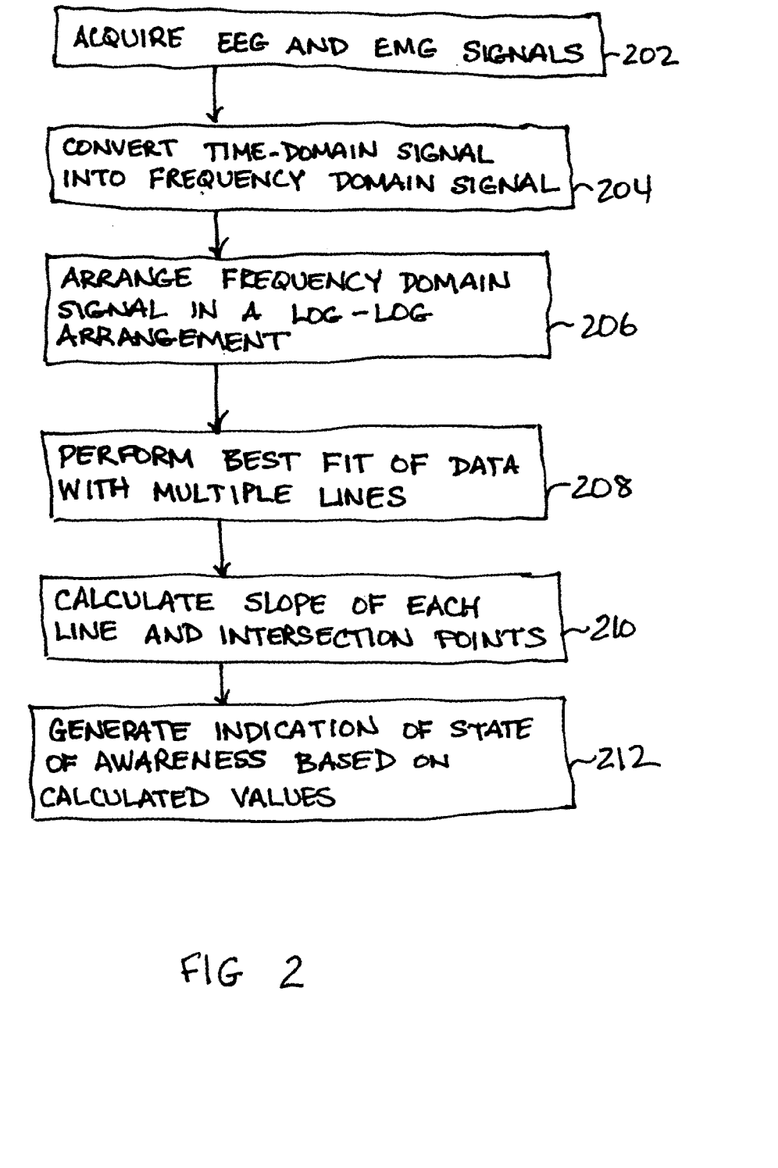
FIG. 2 shows a flowchart of an exemplary algorithm for analyzing EEG spectrograms in accordance with the principles of the present invention.

The flowchart of FIG. 2 depicts an exemplary algorithm for analyzing EEG and EMG spectrograms in accordance with the principles of the present invention. In step 202, the raw EEG signal and EMG signal is captured as is known in the art. For example, signals in the range of approximately 0 to 128 Hz are captured; however, it is contemplated that even higher frequencies may be captured and analyzed as well. Present techniques and devices as well as future-designed EEG and EMG devices may be utilized to acquire the raw signals. Also, as well known in the art, the raw signals may be filtered and processed to reduce noise and to remove artifacts that are known to be introduced into the signals. The raw signal is a time-domain series of samples that are sampled or converted to digital signals which can be then processed by computer platforms or specialized digital signal processors.

Once the digital signals are generated, the time-domain signal can be transformed into a frequency-domain signal in step 204. While there are a number of techniques for converting between the time domain and the frequency domain, a common technique involves the fast Fourier transform method. A number of computationally efficient algorithms for performing fast Fourier transforms beneficially result in a technique that can occur in almost real time with even limited computational power. As one of ordinary skill will recognize, there are a number of parameters that can be selected to control how the transform operates and performs. As an example, in one embodiment of the present invention, a two-second window averaged for periods of about one minute, or even longer, is used to convert the time-domain signal.

One novel realization reached by the present inventor is that the frequency domain signals are visually informative when arranged in a log-log format, in step 206. In particular, the y-axis represents the power, or power spectral density, of a frequency in the signal and the x-axis represent the frequency. Both axes, though, are scaled logarithmically. What results is a visual display that reveals that the resulting frequency-domain data can generally be split into multiple regions—a first region from about 0 to about 10 or 20 Hz, a second region representing the frequencies above the first (to about 40 Hz); and a third region typically associated with EMG signals between about 40 Hz and 130 Hz. The first range can extend further as well, especially when the patient is in a state of awareness These regions will be conveniently referred to a low frequency segment, a high frequency segment, and an EMG segment. Those labels are used as a way of convenience and of comparison to each other and are not intended to limit the segments in any way to a particular range of frequencies.

Once the frequency-domain data points are arranged in this log-log format, a best-fit line is calculated in steps 208. In particular, one or more best fit lines are calculated for each segment. One of the easiest best-fit approaches is to use a least-squares approach but one of ordinary skill will recognize that there are numerous other data regression schemes that may be used to approximate a line while minimizing error. In one example, the best fit lines were accomplished using an iterative least-squares approach where the slope and y-intercept of a line providing the minimum mean square between the log of the spectral magnitude and that line were obtained. Also, one of ordinary skill will recognize that optional methods of fitting the data may be accomplished during the least-squares fit as well. For example, points that are statistical outliers can be discarded if their error size suggests that they should not be used when fitting the data to the best-fit line. The best-fit line can then be recalculated with the outliers ignored As mentioned, different regression methods other the least-squares may be used to calculate the best fit lines and furthermore, one regression method may be used for the high frequency line and a different regression method used for the low frequency line and yet a third regression method may be used for the best fit line of the EMG segment.

The determination of when the best fit lines are complete can be accomplished in a number of different ways. The determination can be based on an event in the EEG or EMG signal itself. For example, the EEG signal may exhibit an alpha-peak at a certain frequency and that value is used for the endpoints of the two best-fit lines of the high and low frequency segments. For example, the first best-fit line is calculated from the lowest frequency to the alpha-peak frequency and the second best-fit line is calculated from the alpha-peak frequency to the highest frequency. The alpha-peak frequency, itself, can be selected in different ways such as at the beginning of the peak, a center frequency, or at the end of the peak. Alternatively, the decision to stop the least-squares fitting can be determined on the fly as the best-fit lines are being calculated. For example, an analysis can be made to determine when a similar frequency is reached from both directions at which both the first best-fit line and the second best-fit line start deviating significantly (e.g., some percentage, such as, for example 3% to 8%) from the previously calculated best-fit line. This frequency, then, is the dividing point between the two best-fit line segments.

Once the best-fit lines are determined, then the slope of each line can be calculated and the intersection point as well with the neighbor segment (see step 210). Of particular interest is the frequency at the intersection point. Based on the relative slopes of the best-fit lines and the frequency of the intersection points, an indication is generated, in step 212, that relates to the state of anesthesia, or the state of awareness, of the patient.

Figure 3:
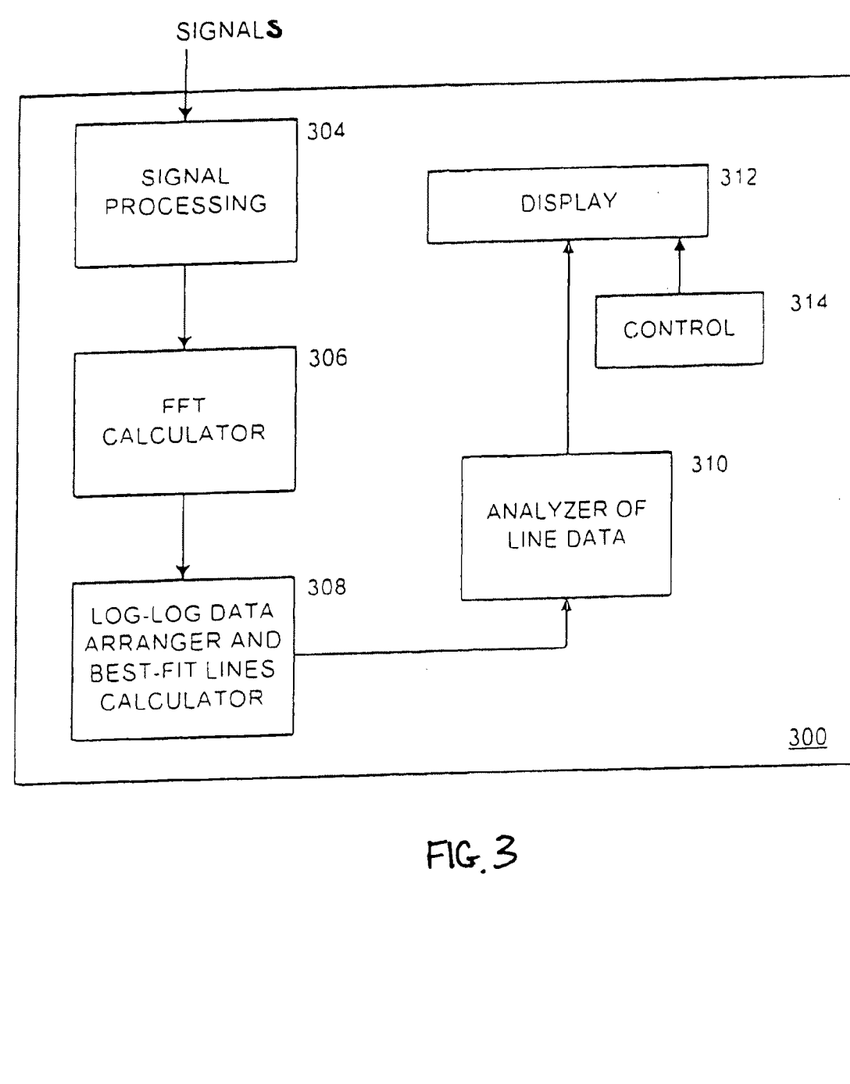
FIG. 3 shows an apparatus on which the flowchart of FIG. 2 may be performed in accordance with the principles of the present invention.

FIG. 3 illustrates an automated platform on which the algorithm described above may be implemented. In practice, the device 300 would be used during surgery to monitor the anesthesia state of the patient to allow an anesthesiologist to modify the delivery of an anesthetic agent as appropriate. The device 300 is shown in functional block form in FIG. 3 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 3.

The EEG and EMG signals 302 are received and then filtered and converted by a signal processor 304. That signal can then be transformed into the frequency domain by a fast Fourier transformer 306. The power spectrum of the frequency domain signal can then be calculated in a log-log arrangement so that an interpolator 308 can calculate multiple best-fit lines for the spectrum. An analyzer 310 analyzes the best fit lines to determine their respective slopes and the frequency at which they intersect.

Based on the calculations of the analyzer 310 a display 312 provides an indication of the anesthesia state of the patient. The display 312 may be multifaceted to provide the viewer of the display with different information. Two particularly relevant pieces of data are a) the difference between the slopes of the best-fit lines and b) the frequency at which the lines intersect. Thus, these values may be displayed as raw numeric information. A graphical display may be included which graphs these values in a historical fashion so that the viewer of the display can see how the values have been changing in some preset time period. For example, the display could show the values over a window depicting the last 5 minutes. A control 314 for the display 312 can be used to allow the viewer to change between different formats of output as desired. The display 312 can also be configured to display the best-fit lines in near real-time with (or without) the additional values discussed above. Also, (not shown) the device 300 may included a storage function that records various signals and calculations during the duration of the surgery.

The alpha peak, discussed above, is not the only peak of interest. Furthermore, there is a pattern to the peaks that changes as anesthetic agent concentration changes or there is surgical stimulation. At high concentration there is 1-2 Hz delta peak and a 4-7 Hz peak. As agent decreases the 1-2 Hz peak eventually disappears unless there is a "paradoxical" response to surgery. Typically, the 4 Hz peak splits into a 4-5 Hz peak and a 6 to 7 Hz peak; as the 6-7 Hz component increases in frequency and amplitude and becomes the alpha peak. When the alpha peak moves out to 8, 9 or 10 Hz the 4 Hz peak may go away. Then the alpha peak moves out to 12 or 14 Hz before the patient wakes up. There can be minor variations on this and responses to surgery will usually prevent the full progression unless an increasing amount of analgesia (anti-pain) is given.

This peak pattern progression is useful to indicate the level of anesthetic agent effect. There is variability of patient sensitivity to anesthetic agents and this progression allows a clinician to adjust the level to the individual patient's response.

Thus, the one or more peaks and their behavior could be used as an index or component of an index indicating brain function. This is contrary to the conventional wisdom that the peaks do not produce a consistent and useful pattern.

The log-log evaluation is very useful to determine if a peak is valid for this method. For example, when the alpha peak is in the low frequency segment, near to the intersection, and there is a steep high frequency slope, then it is almost certain that the patient is not awake.

Thus, we have described a method of determining the level of the anesthetic state by measuring the frequency and amplitude of EEG peaks, or the center frequency, height, and width of EEG peaks after removing a baseline, with a log-log method or other baseline method. In particular, as one example, a method is described for monitoring EEG peaks, especially the "alpha" peak frequency, amplitude, and width for CNS responses to surgical stimulation.

Once measured, the above mentioned peak parameters are used to create an index or otherwise indicate where that pattern of parameters fits on a continuum of such parameters.

The described method and apparatus also includes a display or utilization of the log-log presentation of the EEG and EMG spectrogram out to 130 Hz. This data is approximated with more than two best-fit lines and preferably approximated with four or more best fit lines. The additional lines are a very high frequency (EMG) line (130 Hz down to the high frequency line) and optionally a very low frequency line from 0 to 1 Hz Relevant parameters when evaluating the data are 1) the frequency and amplitude of the intersections and 2) the slopes of the individual lines and the slopes of the lines relative to other lines.

The slope of the high frequency line is believed to be the best parameter to distinguish consciousness from unconsciousness and on down to "light" and then "moderate" anesthesia. After that peak analysis is used to follow changes down to "deeper" anesthesia (present methods are not able to measure depth below "moderate".)

When the EEG-EMG spectrogram is represented in log-log format, its characteristics such as the best-fit lines, their absolute and relative slopes, the points of intersection (frequency and amplitude), the peaks (their center frequency, amplitude and spread), and any other deviations from the best-fit lines that are not "peaks" may be used as a "template" or pattern of data. A template can be calculated for a patient's data and then be compared to a library of templates and used to classify the data. One would want to do that in order to choose between simpler algorithms or combinations of algorithms that provide the best analysis tools for a particular patient. A template is essentially a set of variables and their values derived in part, at least, from the log-log representation of data. More generally, the template can include a range of values for one or more of the variables.

Furthermore, this template approach can be used to compare data for the same patient over time, possibly to warn of impending response to surgery. In general, a template can be used, as explained more fully below, to define boundary regions within one or more of the frequency zones to show how the current data differs or is similar to the template. First, the library of templates can be searched for a template or set of values that closely matches the current data. One of ordinary skill will recognize that there are a variety of ways to perform multivariate pattern recognition to identify candidates from a library that match a current data set. Using these techniques, an appropriate template can be selected. If the current data for a patient changes from matching a template to not matching a template, then that patient has changed. The new best-match template could indicate higher or lower anesthetic agent level or a response to surgical stimulus. This information can be used to alert the observer that impending awareness or some other activity is imminent and needs closer monitoring. If it is determined that no template matches the current data, then the assumptions about what different line slopes and intersection frequencies mean may need to be discarded until the current data once again matches a template in the library.

The templates can be used in a second way to differentiate between two different interpretations of a patient's current data. For example, what is known as the "paradoxical response" and a deep anesthesia state have many similarities in how they appear in a log-log display. However, by including other information such as heart rate and gas concentration in the template, an observer will be able to recognize when the paradoxical response is occurring and when it is not.

The template can be used to draw boxes or regions on the screen or can be used in the background (unseen by the observer) to analyze the data and potentially control the way data is modeled or displayed.

Figure 4:
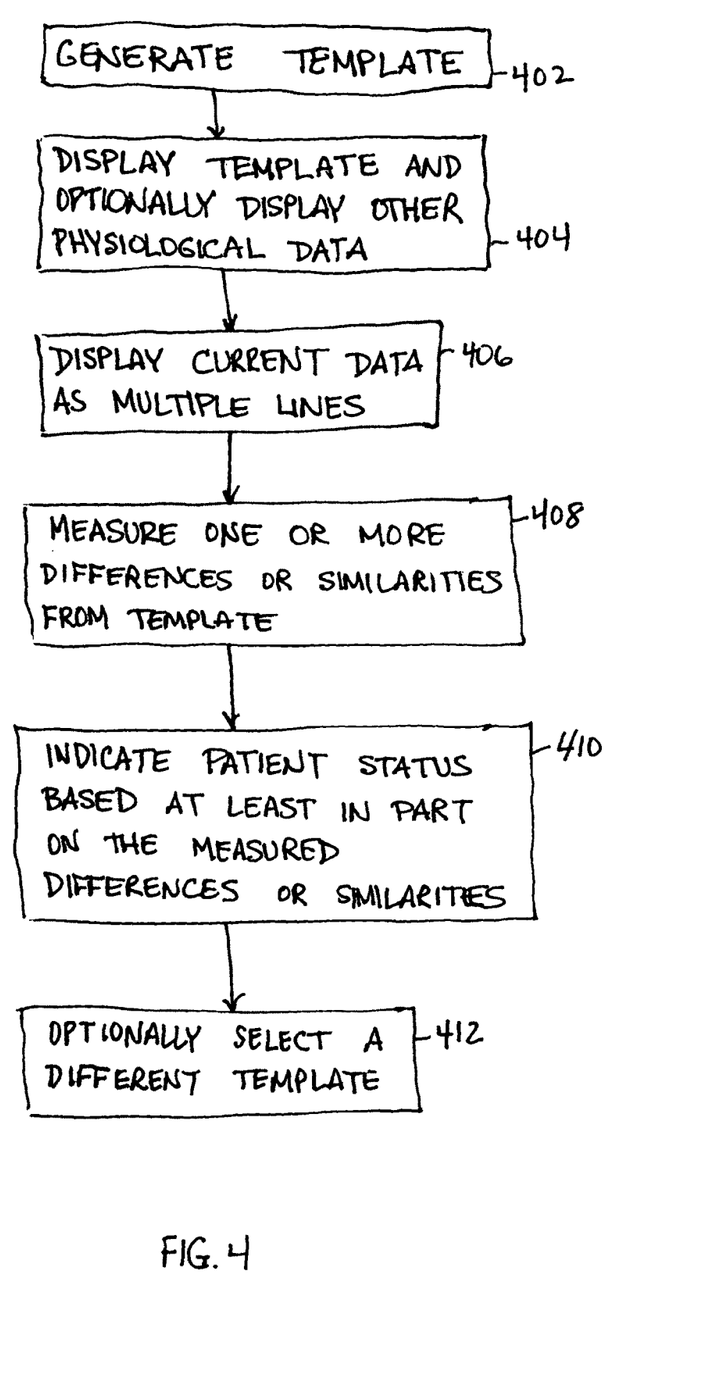
FIG. 4 shows a flowchart of an exemplary algorithm for analyzing EEG and EMG spectrograms in accordance with the principles of the present invention.

FIG. 4 shows a flowchart of a process that includes a template that is useful for indicating patient awareness. In step 402, a template is generated. Generation of a template can be accomplished in a variety of different ways. For example, the template can be a sliding averaging window of the patient's current EEG and EMG data. Alternatively, the template could be selected from historically collected data from this patient in the past, possibly in anticipation of being given anesthesia. If no historical templates are available for a particular patient, then a suitable template could be selected from a library of templates. In particular, the selected template can be chosen based on similarities in age, sex, previous medical history, or the state of intoxication or impairment of the patient. As one of ordinary skill would recognize, the data of the templates can be normalized to account for the different impedances and other variables that occur across the different persons or models used to create various templates. In this way, templates and current data can be accurately compared.

In step 404 and 406, the template may be displayed along with the currently calculated best-fit lines. In addition, a previous best-line model can be displayed such as a snapshot 10 seconds ago or a sliding window average of the best-line models for the patient. If the template is displayed, the differences between the template and the current data can be highlighted so that a viewer can easily distinguish what is happening in near real-time. For example, if the alpha peak is spreading, then the area underneath it could be shown in one color (e.g., green) and if it is shrinking, then it can be shown in another color (e.g., red). If the current line is above the template or another best-line-model, then the area between them can be shown in one color and if the current line is below the template or other best-line model, then the area between them can be displayed in a different color. In this manner, the viewer can more easily determine how the current data differs from the template as well as previous best-line models.

The template that may be displayed can include physiological parameters in addition to the EEG and EMG spectrogram data. Respiration rate, blood pressure, and heart rate can be included in the template as well as can other readings such as information about the anesthesia like the gas concentration. Using this additional physiological data, the template can be cross-referenced with changing physiological data of the patient to more correctly indicate the state of awareness of the patient. As discussed below, there are a number of other patient parameters that can be used in conjunction with the EEG and EMG displays to more fully indicate the state of awareness of a patient.

In step 408, the differences or similarities between the current data and the template are calculated or measured. Not only does the current data itself provide evidence of the state of awareness of the patient, as discussed above regarding the slope of the lines and the intersection frequencies; but the difference of the current data from a template can provide further data that allows an observer to interpret the information and more correctly determine the state of awareness of the patient. In addition to the differences between current data and the template being used, the similarities may be used as well. For example, the amplitude of the lower frequency region of the EEG spectrogram can be compared to a template of an aware person and, if similar, this information can be used to alert an observer that the patient may be becoming aware. Similarities of peak shapes, peak frequencies, line slopes, and line intersection among other information can all be used to determine whether or not the current data is similar to a template of a known awareness state to help determine the present condition of the patient.

Thus, in step 410, an indication of the state of awareness of the patient can be displayed that at least in part is related to the differences or similarities between the current data and the template. Optionally, in step 412, the best-match template that is selected can change over time as the patient's data changes.

Determining a best-match template can be accomplished in many different ways. One method, for example, may be to locate candidate templates with similar intersection point frequency values for the best-fit lines. From this candidate set, templates having matching slopes and then amplitudes could be identified. Once identified, the template could be adjusted or normalized based on several minutes of data to create a custom template once a stable pattern for the patient is observed.

Figure 5:
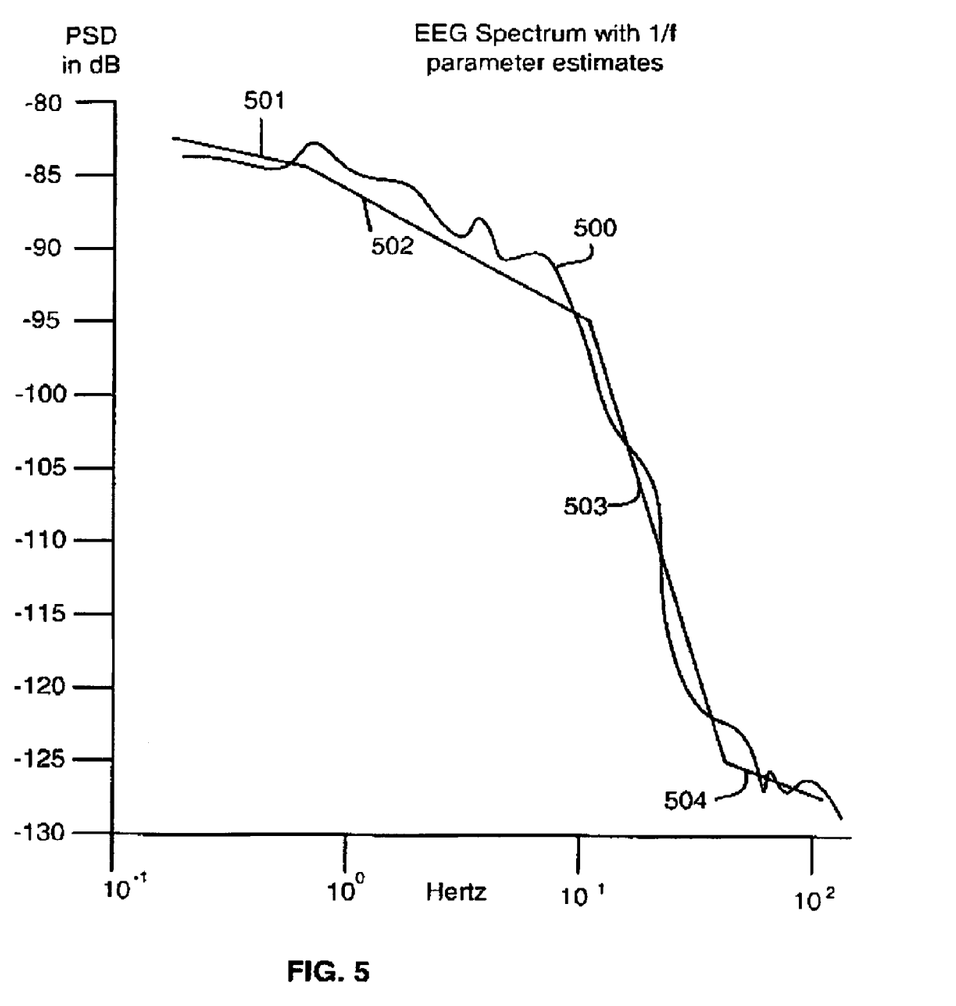
FIG. 5 shows a log-log spectrogram in accordance with the principles of the present invention.

FIG. 5 shows an example EEG and EMG spectrogram 500 in log-log format in accordance with the principles of the present invention. The combined spectrograms have been divided into four regions and each section has been modeled with a best-fit line. The region below about 1 to 2 Hz has a line 501, the lower frequency region of the EEG spectrogram has a line 502, the higher frequency region of the EEG spectrogram has its own line 503, and the EMG frequency region (above about 40 Hz to about 130 Hz) has a best-fit line 504. As discussed above, the relative slopes and intersection points of these lines may be used to determine and indicate the state of awareness of a patient. This example uses four lines but one of ordinary skill will recognize that the data could also be modeled with more or less than four lines without departing from the scope of the present invention.

Figure 6:
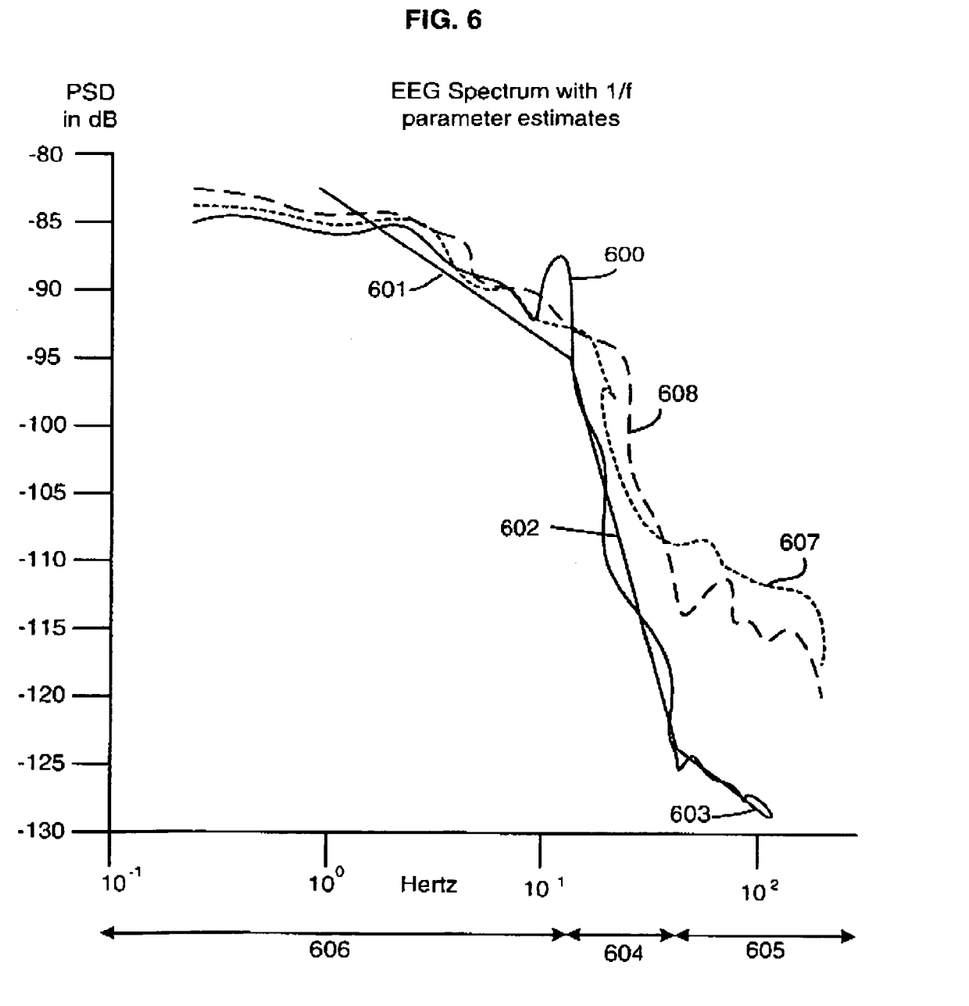
FIG. 6 shows another log-log spectrogram in accordance with the principles of the present invention.

FIG. 6 shows a combined EEG and EMG log-log spectrogram 600 that is modeled with three lines 601, 602 and 603. Also, spectrograms 607 and 608 depict data that includes an EMG response for the same patient. In other words, the data in 607 and 608 show changes above about 40 Hz (region 605) that also extends into region 604 (between about 20 Hz and 40 Hz). The effect of the EMG response in region 605 would cause a significant change in the slope of a best-fit line as compared with best-fit line 602 while the data in the lower frequency region 606 changes very little and the best-fit lines for either spectrograms 607 or 608 would appear similar to 601. Other conventional indicators presently used for measuring depth of anesthesia incorrectly conclude that the spectrograms 607 or 608 indicate a patient is aware or is becoming aware. This is mostly due to the effect the EMG response has on the sensed data in the higher frequency region 604. However, using the present log-log display, an observer can see that the data in region 606 barely changes and that the data in the region 604 is likely just an extension of the EMG response that is clearly shown in the region 605. As a result, even though there is some change of the displayed graph, it can be correctly interpreted that the patient remains in an unaware state.

FIG. 6 happens to show three zones or regions 604, 605 and 606. These zones can be fixed in that zone 606 includes frequencies from about 0 Hz to about 20 Hz, while zone 604 includes frequencies from about 20 Hz to about 40 Hz, and zone 605 includes frequencies from about 40 Hz to about 130 Hz. These zones could also be data dependent in that they could be defined by the intersection frequencies of the best-fit lines 601, 602 and 603. When implemented in an apparatus that includes a display, the display interface can allow the observer to set the frequency ranges for the zones and also whether to display one, two or all three zones.

The frequency ranges and the three or four different zones discussed above are typical for halogenated inhalation agent anesthesia. However, more exotic methods (e.g., ketamine, total IV, large dose opioid, etc.) can have different intersection points, slopes and amplitudes. Accordingly, consideration of more than three frequency ranges is beneficial as well as ranges that are not considered to transition at 20 Hz and 40 Hz as discussed above. For that reason, the templates used when comparing data can also be based on the particular anesthesia being supplied to the patient. Not only will an observer be able to see how a patient's data is changing but he will also be able to compare it with a known template for the given anesthesia being applied. In this way, a quicker and more accurate determination of the state of awareness for the patient can be made.

Figure 7:
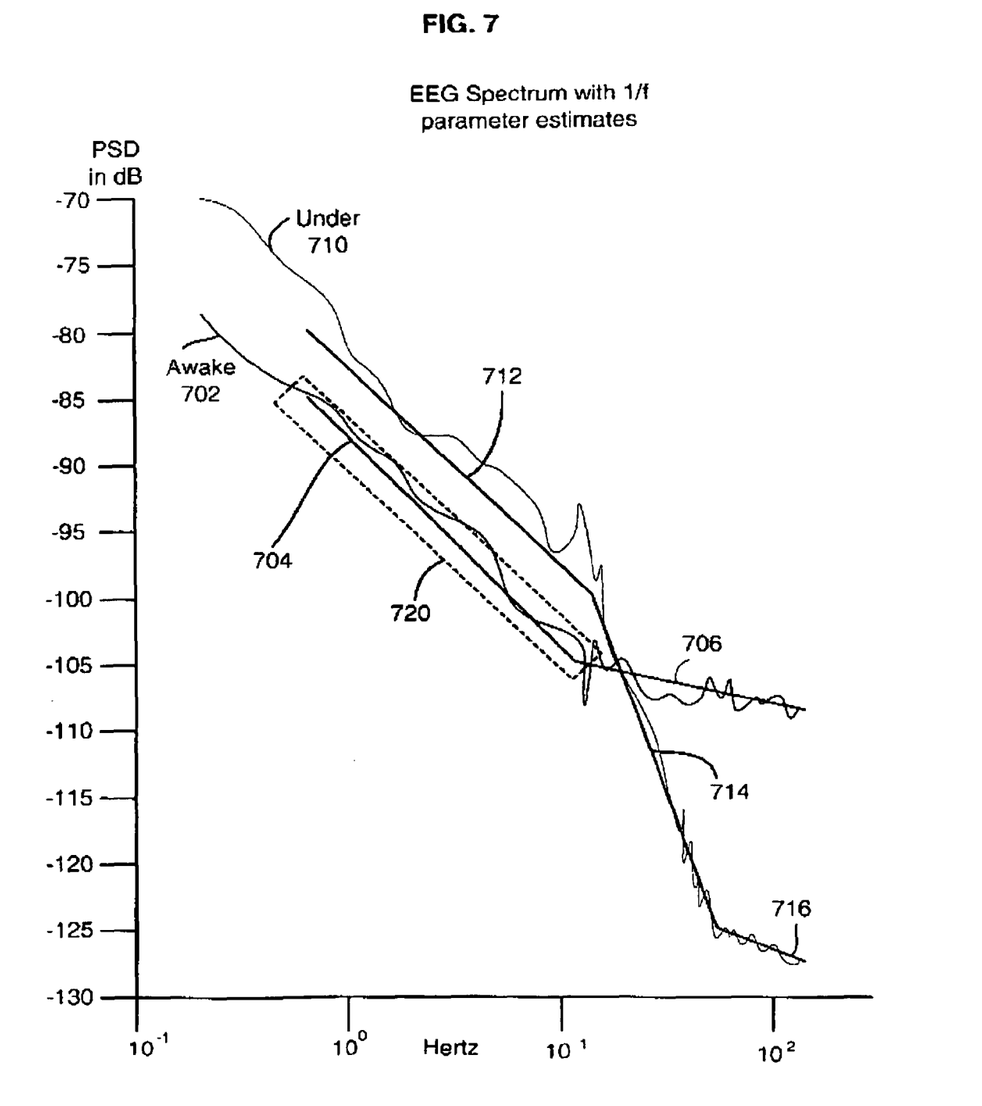
FIG. 7 shows yet another log-log spectrogram in accordance with the principles of the present invention.

FIG. 7 shows two different patterns that can be observed in the combined EEG and EMG spectrograms presented in a log-log format. An awake spectrogram 702 is modeled with lines 704 and 706 while an unaware spectrogram is illustrated by 710 and modeled with lines 712, 714 and 716. The difference in slope of line 714 and 706, in particular, can be used to determine, and therefore indicate, the state of awareness of a patient.

One potential aspect of a template is shown in FIG. 7 as the box 720 that surrounds the lower frequency best-fit line 704. This template can include a box that is positioned and sized based on previously calculated or sensed data. This box is shown as a rectangle but can be other shapes as well and is used to define a region, or neighborhood, around the best-fit line 704. A similar type of box can be used within the templates for the other frequency regions as well. However, the example box 720 is used to help illustrate that if the changing best-fit line from line 704 to line 712 is inside or outside the box 720, then a conclusion can be made about the state of the patient. For example, an EEG from awake to unconsciousness is typically characterized by an increase in the amplitude of the low frequency waves and a decrease in the amplitude of the higher frequency waves (as illustrated in FIG. 7). Because is it easy to visually determine, or to automatically detect, that the best-fit line 712 is outside the box 720, an observer can be substantially certain that the patient is no longer in an aware state based on the log-log graph of FIG. 7.

In addition to the peak parameters discussed above, the "pattern" of peaks can be used as an indication of the patient's state. Also changes in peak parameters and peak patterns that occur as other patient variables change could be used in combination for a more robust and accurate indicator of brain function.

For example, when the pulse rate goes up and down in response to surgical manipulation the EEG parameters can change in at least two different patterns: 1) pulse rate up: Alpha peak frequency, amplitude, and or spread up while delta peak amplitude goes down; and 2) pulse rate up: delta peak amplitude goes up and alpha amplitude or frequency goes down. In addition to peak changes, there may also be changes in the best-fit line slopes and intersection frequencies. For example, when the paradoxical response is extreme the intersection moves to a very low frequency and the slope of the high frequency best-fit line becomes much less steep. The result would be that the difference between the before and after best-fit lines would be a large triangle.

Thus, a "smart monitor" is contemplated that has multiple input streams of data from the standard or new monitors and also the EEG and EMG parameters discussed above. The device matches the pattern and changes in pattern and values with either a database of patterns, or set of rules, or an algorithm to make an assessment, association, and provide information that none of the single monitored points could make. It is beneficial not to simply display the original parameters, but instead to identify the pattern and report any relevant information. Thus the apparatus evaluates and displays new parameters such as cardiovascular variability, arousal response level, stress response, or intrinsic analgesic response.

In addition to the log-log display and best-fit line approach discussed above, EEG spectrogram peaks during anesthesia for surgery occur at frequency ranges and agent concentrations that are consistent with thalamic oscillations that are well understood. This finding suggests that EEG spectrogram peaks during anesthesia are related to specific thalamic mechanisms and provide a method for monitoring progressive hyper-polarization of thalamic neurons as a halogenated anesthetic agent concentration is increased.

From the EEG data being collected, the peaks and troughs can be located by going from about 0.5 Hz to about 20 Hz in either direction. For example, the peaks and troughs of the EEG signal can be determined by calculating the first and second derivative of the power (or amplitude, or log of power) versus linear frequency. These calculations can be accomplished in addition to, or as an alternative of, calculating the best-fit lines in this frequency region. This information can be used to determine if changes in the patient's data may, for example, be from an EMG response rather than from lack of anesthesia. If the best fit lines change in the higher frequency region of the EEG or the EMG frequency region, but no significant changes occur with the peaks or their pattern in the 12 Hz and below region, then any observed change in the patient's data may confidently be attributed to an EMG response. Also, the first derivative will identify the intersection of the two log-log lines because the amplitude rolls off at that point.

Additionally, separate from the log-log best-fit lines, the pattern of peaks that are determined between about 0 Hz and 20 Hz also provides useful information about the state of awareness of a patient. As discussed above, a deeply anesthetized patient may typically have a peak around 1 Hz and another peak around 5 Hz and, then as the anesthetic agent concentration is reduced the 5 Hz peak splits. As the agent is further reduced the alpha peak shifts to higher and higher frequency and typically occurs between about 10 Hz and 12 Hz. Typically, there are two peaks at high agent concentration and in other states of awareness there can be three or more peaks. In contrast, during an extreme paradoxical response, there is typically only a single peak present.

By detecting the peaks and their patterns in this frequency range, an observer can determine a state of awareness for the patient. Similarly, for automated equipment, an indicator (such as a light or a graph) can be displayed to indicate whether the detected pattern of peaks indicates the patient is in an aware or an unaware state. The pattern of peaks can include information such as their center frequencies, their amplitudes, and their widths (or the widths of the troughs). Additionally, the peaks and their patterns can be correlated with other information such as, for example, heart rate or gas concentration in order to provide even more confidence to an observer about what the data is revealing about the patient's condition.

Figure 8:
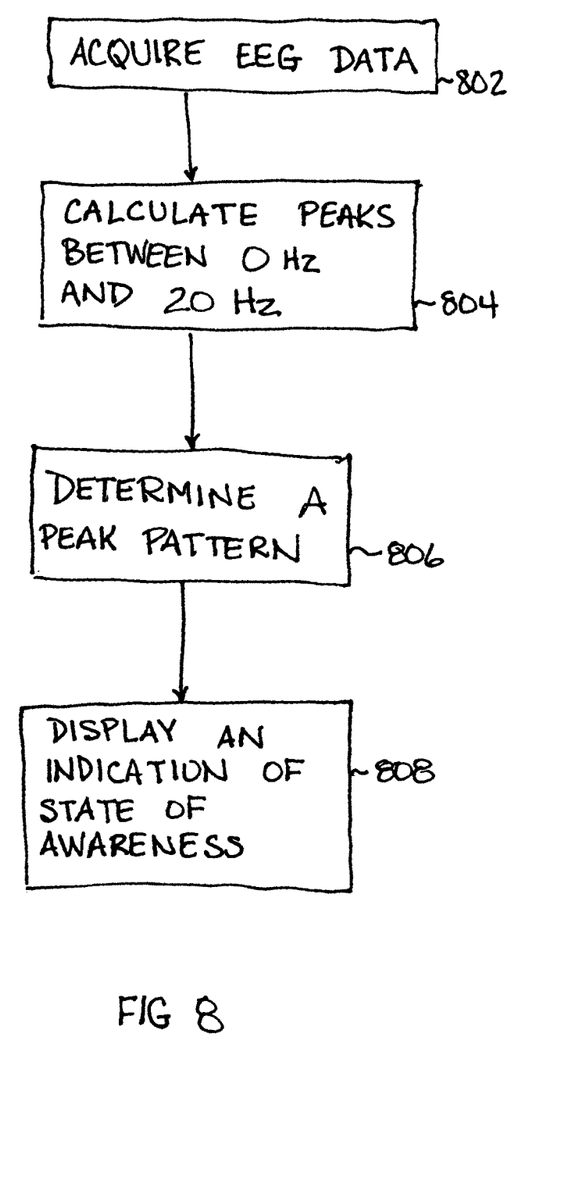
FIG. 8 shows a flowchart of an exemplary method of indicating a patient's state of awareness based on a pattern of EEG peaks in accordance with the principles of the present invention.

FIG. 8 illustrates a flowchart of the above discussed method for determining and indicating the awareness of a patient. In step 402 the EEG signal is acquired. The data can be filtered, digitized, or otherwise manipulated if desired in order to clean-up the signal before being used in subsequent calculation. Next, in step 804, the peaks between about 0 Hz and about 20 Hz are calculated. A variety of different software and hardware combinations may be used to implement a calculator for determining the peaks in the signal, the amplitudes at those peaks, and the frequencies and widths of those peaks. This information about the peaks is used to identify a peak pattern, in step 806. Based on the pattern, an indicator can then be displayed, in step 808, that provides an indication of the brain function of a patient.

In the above examples and discussions the data and its analysis were considered in the frequency domain. However, one of ordinary skill will readily recognize that analogous time domain analysis may be performed without departing from the scope of the present invention. Also, if time-domain analysis of the data is performed, then appropriate filtering and signal conditioning techniques may be used to simplify the analysis and improve its accuracy.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for providing an indication of a state of awareness for a patient, comprising the steps of:
   arranging data of an EEG and EMG power spectrogram to provide power versus frequency in a log-log arrangement;
   calculating a first best-fit line for a lower frequency region of the EEG power spectrogram, using a processor;
   calculating a second best-fit line for a higher frequency region of the EEG power spectrogram, using a processor;
   calculating a third best-fit line for the EMG power spectrogram, using said processor; and
   displaying, on a display device, an indication of the state of awareness based on the first, second and third best-fit lines.

2. The method of claim 1, further comprising the steps of:
   acquiring an analog time-domain EEG signal; and
   acquiring an analog time-domain EMG signal;
   converting the analog time-domain EEG signal into a digital time-domain EEG signal; and
   converting the analog time-domain EMG signal into a digital time-domain EMG signal.

3. The method of claim 2, further comprising the steps of:
   transforming the digital time-domain EEG signal to a frequency-domain EEG signal;
   transforming the digital time-domain EMG signal to a frequency-domain EMG signal;
   calculating the EEG power spectrogram based on the frequency-domain EEG signal; and
   calculating the EMG power spectrogram based on the frequency-domain EMG signal.

4. The method of claim 1, further comprising:
   calculating a fourth best-fit line for frequencies below about 2 HZ in the lower frequency region of the EEG power spectrogram.

5. The method of claim 1, wherein the first and second best-fit lines intersect at an intersection frequency.

6. The method of claim 5, further comprising:
   calculating a first slope of the first best-fit line and a second slope of the second best-fit line.

7. The method of claim 6, wherein the indication is determined based, at least in part, on a difference between the first and second slopes.

8. The method of claim 7, wherein the indication is determined, at least in part, on the intersection frequency.

9. The method of claim 1, wherein the step of displaying further includes the steps of:
displaying the first, second, and third best-fit lines in a near real time manner.

10. The method of claim 1, wherein the step of displaying further includes:
receiving input to control the display to select from among different display formats.

11. The method of claim 1, wherein the indication indicates one of REM sleep, non-REM sleep, and awakeness.

12. The method of claim 1 wherein the EEG and EMG spectrograms include frequencies from about 0 Hz to about 130 Hz.

13. An apparatus for providing an indication of a state of awareness for a patient, comprising:
a data formatter configured to arrange data of an EEG power spectrogram and EMG power spectrogram, that provides power versus frequency, in a log-log arrangement;
a first calculator configured to calculate a first best-fit line for a lower frequency region of the EEG power spectrogram;
the first calculator also configured to calculate a second best-fit line for a higher frequency region of the EEG power spectrogram;
the first calculator also configured to calculate a third best-fit line for a region of the EMG power spectrogram; and
a display configured to provide an indication of the state of awareness based on the first, second and third best-fit lines.

14. The apparatus of claim 13 wherein the EEG and EMG spectrograms include frequencies from about 0 Hz to about 130 Hz.

15. The apparatus of claim 13, further comprising:
an analyzer configured to calculate an intersection frequency of the first and second best-fit lines, a first slope of the first best-fit line, and a second slope of the second best-fit line.

16. The apparatus of claim 15, wherein the indication is based, at least in part, on a difference between the first and second slopes and the intersection frequency.

17. The apparatus of claim 15, wherein the analyzer is configured to calculate an intersection frequency of the second and third best-fit lines, and a third slope of the third best-fit line.

18. The apparatus of claim 13, wherein the first calculator also configured to calculate a fourth best-fit line for a frequency region below the lower frequency region of the EEG power spectrogram.

19. The apparatus of claim 13, wherein the indication indicates one of REM sleep, non-REM sleep, and awakeness.

20. A method for providing an indication of a state of awareness for a patient, comprising the steps of:
generating a template, the template representing a state of awareness;
arranging data of a EEG and EMG power spectrogram to provide power versus frequency in a log-log arrangement for frequencies from about 0 Hz to about 130 Hz;
calculating a first best-fit line for a lower frequency region of the EEG power spectrogram, using a processor;
calculating a second best-fit line for a higher frequency region of the EEG power spectrogram, using said processor;
calculating a third best-fit line for a frequency region of the EMG power spectrogram, using said processor
comparing one or more of the first, second, and third best-fit lines with the template to determine a difference; and
displaying, on a display device, an indication of the state of awareness based on the difference.

21. The method of claim 20, wherein generating a template includes:
averaging previous spectrogram data for the patient for a predetermined time period.

22. The method of claim 20, wherein generating a template includes:
selecting the template from a plurality of previously acquired spectrogram templates related to the patient.

23. The method of claim 20, wherein generating a template includes:
selecting the template from a plurality of spectrogram templates related to person physiologically similar to the patient.

24. The method of claim 20, wherein the template includes physiological parameters in addition to the EEG and EMG spectrogram.

25. The method of claim 24, wherein the difference relates to one or more of an area under an alpha peak, a center frequency of the alpha-peak, a slope of the first best-fit line, a slope of the second best-fit line, a slope of the third best-fit line, an intersection frequency of the first and second best-fit line; and the physiological parameters.

* * * * *